United States Patent [19]
Tomita

[11] Patent Number: 5,301,675
[45] Date of Patent: Apr. 12, 1994

[54] APPARATUS FOR MEASURING BLOOD FLOW VELOCITY AND BLOOD FLOW VOLUME IN AORTAS

[76] Inventor: Mitsuei Tomita, 407 Yamanote Villa Porte, 109 Yamanote-Cho, Naka-Ku, Yokohama 231, Japan

[21] Appl. No.: 834,253
[22] PCT Filed: Jun. 19, 1990
[86] PCT No.: PCT/JP90/00813
§ 371 Date: Feb. 11, 1992
§ 102(e) Date: Feb. 11, 1992
[87] PCT Pub. No.: WO91/19451
PCT Pub. Date: Dec. 26, 1991

[51] Int. Cl.⁵ .............................. A61B 5/00
[52] U.S. Cl. ..................... 128/672; 128/677; 128/687; 128/686
[58] Field of Search ........ 128/677, 678, 679, 680-684, 128/687-692

[56] References Cited
U.S. PATENT DOCUMENTS

| | | | |
|---|---|---|---|
| 3,908,640 | 9/1975 | Page | 128/2.05 T |
| 4,245,648 | 1/1981 | Trimmer | 128/680 |
| 4,396,018 | 8/1983 | Sibley | 128/680 |

FOREIGN PATENT DOCUMENTS 50-33676 3/1975 Japan.

OTHER PUBLICATIONS

Application Ser. No. 521,156, dated Jun. 1991, Tomita.

Primary Examiner—Lee S. Cohen
Assistant Examiner—Robert L. Nasser, Jr.
Attorney, Agent, or Firm—Ladas & Parry

[57] ABSTRACT

A cuff (200) is put around an upper arm and a blood flow shutting bag (220) thereof shuts the blood flow at the upper arm. A forward detection bag (210) is disposed upstream and a rear detection bag (230) is disposed downstream of the blood flow shutting bag. A forward sensor (110) and a rear sensor (120) are provided to detect pressures in these bags. The sensors respectively detect a forward pulse wave (Wf) and a rear pulse wave (Wb). A reference internal pressure of the cuff is controlled by an air pump (140) and a leak valve (150) controlled by a CPU (130). The pulse waves are monitored to retain the reference internal pressure at a systolic pressure SP and a diastolic pressure DP. A propagation velocity of a pulse wave clearing the cuff retained at the systolic pressure SP can be given based on a delay time SPdt of the rear pulse wave with respect to the forward pulse wave. This propagation velocity is approximate to a blood flow velocity VH of the aorta in a high pressure period. A blood flow velocity VL in a low pressure period is given by dividing the blood flow velocity VH by a set coefficient R. A pulse wave obtained when the reference internal pressure is retained at the diastolic pressure DP is an approximate aortic wave. Based on this approximate aortic wave, blood flow effective sectional areas SH, SL are given.

7 Claims, 10 Drawing Sheets

APPARATUS FOR MEASURING BLOOD FLOW VELOCITY AND BLOOD FLOW VOLUME IN AORTAS

TECHNICAL FIELD

This invention relates to an apparatus for measuring a blood flow velocity and a blood flow volume of an aorta, specifically an apparatus for detecting a passage of a pulse wave by a cuff put around an upper arm, and, based on this detection result, obtaining a blood flow velocity and a blood flow volume of the aorta.

BACKGROUND ART

For the diagnosis of circulation diseases it is effective to measure the blood flow velocity of an aorta and the blood flow volume thereof in addition to electrocardiogram measurement, blood flow measurement, pulse wave analyses, so on. A method which has been conventionally used for measuring blood flow velocity and blood flow volume of aortas is blood vessel catheter measuring method in which a catheter is inserted into an aorta. In this method, a pair of pressure sensors are attached at a set interval to the leading end of the catheter. The catheter is inserted until its leading end reaches an aorta under X-ray inspection to detect pulse waves as a pressure change by both pressure sensors, whereby a blood flow velocity of the aorta is obtained based on a phase difference of the detected pulse waves. A blood flow volume is given by multiplying a blood flow effective sectional area of the aorta by the blood flow velocity. In a different practiced method, a reagent is poured from the leading end of the catheter to measure a lung circulation time of the reagent, whereby an averaged stroke volume per minute is given.

But these invasive blood vessel catheter measuring methods are large scaled by inserting a catheter into an aorta, which unpreferably much burdens patients physically and mentally. An additional problem is that the measuring apparatus is accordingly expensive and is not easily operable for the measurement and requires special skill. Further another problem of the method in which a reagent is poured is that the poured reagent burdens patients.

DISCLOSURE OF THE INVENTION

An object of this invention is to provide an apparatus for measuring the blood flow velocity and blood flow volume of an aorta by a non invasive and simple method.

A first feature of the present invention relates to an apparatus for measuring a blood flow velocity in an aorta, comprising:

a cuff including three bags of a blood flow shutting bag for shutting a blood flow of an upper arm, a forward detection bag for detecting a pulse wave heading to the blood flow shutting bag, and a rear detection bag for detecting a pulse wave which has cleared the blood flow shutting bag;

pressure control means for retaining a reference internal pressure of the blood flow shutting bag and the respective detection bags at a systolic pressure SP;

a forward sensor for detecting as a forward pulse wave a pressure change generated in the forward detection bag;

a rear sensor for detecting as a rear pulse wave a pressure change generated in the rear detection bag with a delay time SPdt from a detection time of the forward pulse wave;

calculating means for dividing a distance L between the forward detection bag and the rear detection bag by the delay time SPdt to obtain a quotient, and outputting the quotient as a blood flow velocity VH of an aorta in a high pressure period.

A second feature of the present invention relates to an apparatus for measuring a blood flow velocity according to the first feature, in which there is further provided means for obtaining a systolic pressure SP, a diastolic pressure DP, a dicroticnotch pressure DNP, calculating a coefficient R based on Equation $R=(SP-DP)/(DNP-DP)$, calculating a quotient by dividing the blood flow velocity VH in the high pressure period by the coefficient R, and outputting the quotient as a blood flow velocity VL in the aorta in a low pressure period.

A third feature of the present invention relates to an apparatus for measuring a blood flow velocity in an aorta, comprising:

a cuff including three bags of a blood flow shutting bag for shutting a blood flow of an upper arm, a forward detection bag for detecting a pulse wave heading to the blood flow shutting bag, and a rear detection bag for detecting a pulse wave which has cleared the blood flow shutting bag;

a forward sensor for detecting as a forward pulse wave a pressure change generated in the forward detection bag;

a rear sensor for detecting as a rear pulse wave a pressure change generated in the rear detection bag with a delay time dt from a detection time of the forward pulse wave;

pressure control means for gradually decreasing a reference internal pressure of the blood flow shutting bag and the respective detection bags from a sufficiently high pressure for shutting a blood flow, retaining the reference internal pressure as a pressure SP when the rear sensor detects a rear pulse wave for a first time; and means for, while the pressure control means is retaining the reference internal pressure at the pressure SP, obtaining a delay time SPdt of the rear pulse wave with respect to the forward pulse wave, calculating a quotient by dividing a distance L between the forward detection bag and the rear detection bag by the delay time SPdt, and outputting the quotient as a blood flow velocity VH of the aorta in a high pressure period.

A fourth feature of the present invention relates to an apparatus for measuring a blood flow velocity in an aorta, comprising:

a cuff including three bags of a blood flow shutting bag for shutting a blood flow of an upper arm, a forward detection bag for detecting a pulse wave heading to the blood flow shutting bag, and a rear detection bag for detecting a pulse wave which has cleared the blood flow shutting bag;

a forward sensor for detecting as a forward pulse wave a pressure change generated in the forward detection bag;

a rear sensor for detecting as a rear pulse wave a pressure change generated in the rear detection bag with a delay time dt from a detection time of the forward pulse wave;

agreement judging means for delaying the forward pulse wave by the delay time dt to superpose the forward pulse wave on the rear pulse wave, and judging whether or not lower parts of both the pulse waves agree with each other with a set precision;

pressure control means for gradually decreasing a reference internal pressure of the blood flow shutting bag and the respective detection bags from a sufficiently high value for shutting a blood flow, retaining the reference internal pressure as a pressure SP during a first period when the rear sensor detects a rear pulse wave for the first time, gradually decreasing the reference internal pressure after the first period of time is over, and retaining the reference internal pressure as a pressure DP during a second period when the agreement judging means agrees;

means for obtaining a delay time SPdt of the rear pulse wave with the forward pulse wave in the first period, dividing a distance L between the forward detection bag and the rear detection bag by the delay time SPdt to calculate a quotient, and outputting the quotient as a blood flow velocity VH of the aorta in a high pressure period; and means for recognizing a rear pulse wave detected by the rear sensor in the second period as an approximate aortic wave near a heart, obtaining a systolic pressure SP, a diastolic pressure DP and a dicroticnotch pressure DNP based on the approximate aortic wave, calculating a coefficient R based on Equation $R=(SP-DP)/(DNP-DP)$, calculating a quotient by dividing the blood flow velocity VH in the high pressure period by the coefficient R, and outputting the quotient as a blood flow velocity VL of the aorta in a low pressure period.

A fifth feature of the present invention relates to an apparatus for measuring a blood flow volume in an aorta, comprising:

a cuff including three bags of a blood flow shutting bag for shutting a blood flow of an upper arm, a forward detection bag for detecting a pulse wave heading to the blood flow shutting bag, and a rear detection bag for detecting a pulse wave which has cleared the blood flow shutting bag;

pressure control means for retaining a reference internal pressure of the blood flow shutting bag and the respective detection bags at a systolic pressure SP and a diastolic pressure DP;

a forward sensor for detecting as a forward pulse wave a pressure change generated in the forward detection bag;

a rear sensor for detecting as a rear pulse wave a pressure change generated in the rear detection bag with a delay time dt from a detection time of the forward pulse wave;

means for obtaining a delay time SPdt of the rear pulse wave with the forward pulse wave when the reference internal pressure is retained at the systolic pressure SP, dividing a distance L between the forward detection bag and the rear detection bag by the delay time SPdt to calculate a quotient, and giving the quotient as a blood flow velocity VH of the aorta in a high pressure period; and means for recognizing a rear pulse wave detected when the reference internal pressure is retained at the diastolic pressure DP as an approximate aortic wave, obtaining a blood flow effective sectional area SH of the aorta in the high pressure period based on a waveform of the approximate aortic wave before a dicroticnotch, and multiplying the blood flow velocity VH in the high pressure period with the blood flow effective sectional area SH in the high pressure period to give a blood flow volume in the high pressure period.

A sixth feature of the present invention relates to an apparatus according to the fifth feature, in which there is further provided means for obtaining a systolic pressure SP, a diastolic pressure DP, and a dicroticnotch pressure DNP based on the recognized approximate aortic wave, calculating a coefficient R based on Equation $R=(SP-DP)/(DNP-DP)$, dividing the blood flow velocity VH in the high pressure period by the coefficient R to calculate a blood flow velocity VL of the aorta in a low pressure period, obtaining a blood flow effective sectional area SL of the aorta in the low pressure period based on a waveform of the approximate aortic wave after the dicroticnotch, and multiplying the blood flow velocity VL in the low pressure period with the blood flow effective area SL in the low pressure period to give a blood flow volume in the low pressure period.

A seventh feature of the present invention relates to an apparatus for measuring a blood flow volume in an aorta, comprising:

a cuff including three bags of a blood flow shutting bag for shutting a blood flow of an upper arm, a forward detection bag for detecting a pulse wave heading to the blood flow shutting bag, and a rear detection bag for detecting a pulse wave which has cleared the blood flow shutting bag;

a forward sensor for detecting as a forward pulse wave a pressure change generated in the forward detection bag;

a rear sensor for detecting as a rear pulse wave a pressure change generated in the rear detection bag with a delay time dt from a detection time of the forward pulse wave;

agreement judging means for delaying the forward pulse wave by the delay time dt to superpose the forward pulse wave on the rear pulse wave, and judging whether or not lower parts of both the pulse waves agree with each other with a set precision;

pressure control means for gradually decreasing a reference internal pressure of the blood flow shutting bag and the respective detection bags from a sufficiently high value for shutting a blood flow, retaining the reference internal pressure as a pressure SP during a first period when the rear sensor detects a rear pulse wave for the first time, gradually decreasing the reference internal pressure after the first period of time is over, and retaining the reference internal pressure as a pressure DP during a second period when the agreement judging means agrees;

means for obtaining a delay time SPdt of the rear pulse wave with the forward pulse wave in the first period, dividing a distance L between the forward detection bag and the rear detection bag by the delay time SPdt to calculate a quotient, and outputting the quotient as a blood flow velocity VH of the aorta in a high pressure period; and means for recognizing a rear pulse wave detected by the rear sensor in the second period as an approximate aortic wave near a heart, obtaining a systolic pressure SP, a diastolic pressure DP and a dicroticnotch pressure DNP based on the approximate aortic wave, calculating a coefficient R based on Equation $R=(SP-DP)/(DNP-DP)$, calculating a quotient by dividing the blood flow velocity VH in the high pressure period by the coefficient R, and outputting the quotient as a blood flow velocity VL of the aorta in a low pressure period;

means for obtaining a blood flow effective sectional area SH of the aorta in the high pressure period based on a waveform of the approximate aortic wave before a dicroticnotch, and multiplying the blood flow velocity VH in the high pressure period with the blood flow effective sectional area SH in the high pressure period to give a blood flow volume in the high pressure period; and means for obtaining a blood flow effective sectional area SL of the aorta in the low pressure period based on the waveform of the approximate aortic wave after the dicroticnotch, and multiplying the blood flow velocity VL in the low pressure period with the blood flow effective sectional area SL in the low pressure period to give a blood flow volume in the low pressure period.

BEST MODE FOR CARRYING OUT THE INVENTION

1. Object to be Measured

Figure 1:
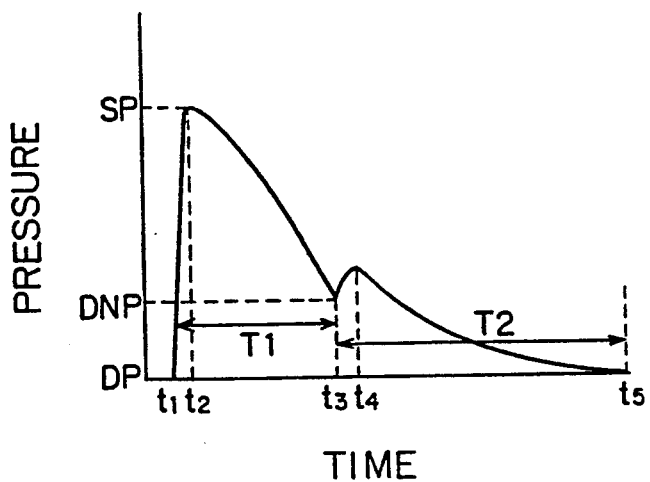
FIG. 1 is a graph of a general waveform of an aortic wave.

The apparatus according to this invention is for measuring the blood flow velocity and blood flow volume of an aorta, and its primary characteristic lies in detecting pulse waves non invasively and obtaining a blood flow velocity and blood flow volume, based on the detected information. First, the pulse waves will be explained. FIG. 1 shows the general waveform of pulse waves (aortic waves) observed in the aortas. As shown in FIG. 1, the waveform is shown by taking time on the horizontal axis and pressures on the vertical axis. The waveform of aortic waves is indicative of blood pressure changes near the heart, and represents a motion of the left ventricular myocardium as it is. This waveform gives very significant information for the diagnosis of circulatory diseases. That is, from the time t1 to the time t2 in FIG. 1 the heart contracts, raising the pressure of the aorta up from a diastolic pressure DP to a systolic pressure SP. Subsequently the heart expands at the time t2. Resultantly from the time t2 to the time t3 a pressure of the aorta is decreased, but since the aortic valve closes at the time t3, a peak takes place. Resultantly a trough called dicroticnotch occurs at the time t3. The pressure at the time t3 is called dicroticnotch pressure DNP. After the time t4 the pressure is slowly decreased back to the diastolic pressure DP at the time t5. The process from the time t1 to the time t5 is periodically repeated every pulse of the heart. In this specification, the period from the time t1 to the time t3 in which the aortic valve opens is called high pressure period T1, and the period from the time t3 to the time t5 in which the aortic valve closes is called low pressure period T2.

Figure 2:
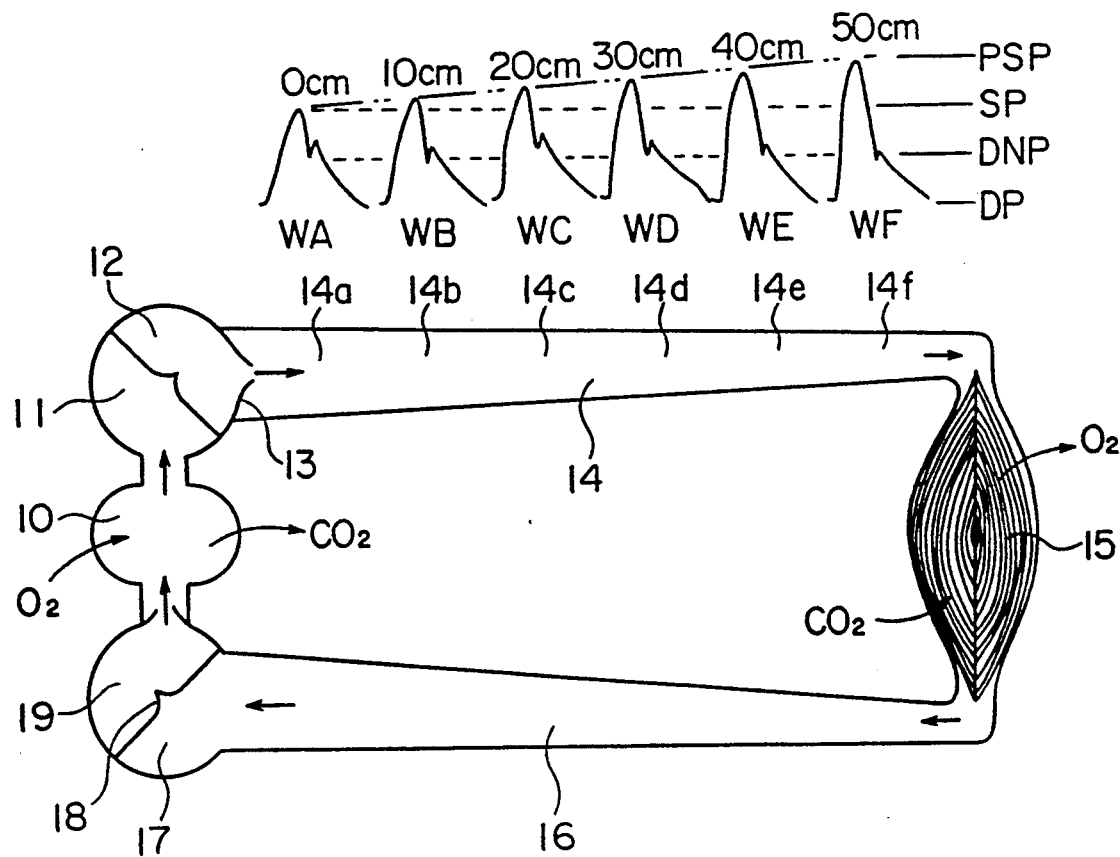
FIG. 2 is a view of the blood circulation passage and a view of a waveform of pulse waves at parts of the passage.

FIG. 2 shows a model of the circulation passage of the blood. The blood which has taken in air in the lung 10 enters the left ventricle 12 from the left atrium 11 to be sent out into the arteries 14 through the aortic valve 13. This blood passes through the peripheral vessels 15 to supply the oxygen to cells, taking in carbon dioxide. Then the blood passes through the veins 16 and then into the right atrium 17 and the valvular tricuspidalis 18 back to the lung 10 from the right ventricle 19 to discharge the carbon dioxide and take in oxygen. This is the circulation passage of the blood. A pressure change in the arteries 14 is a pulse wave. The pulse wave varies depending on detection locations. The pulse wave varies depending on detection locations. The pulse waves WA to WF shown upper in FIG. 2 are those detected at locations along a 0 to 50 cm length of the artery from the heart. At the aorta 14a the pulse wave is a pulse wave WA and corresponds to the aortic wave of FIG. 1. The pulse wave is detected as pulse waves WB to WE respectively at locations 14b to 14e of the artery. At a location 14f nearest to the periphery the pulse wave has the waveform having an increased high frequency component as the pulse wave WF. Accordingly the peak value of the pulse wave WF or peripheral systolic pressure PSP is higher than a systolic pressure SP.

The blood flow velocity and blood flow volume to be measured by the apparatus according to this invention are blood flow velocity and blood flow volume in the aorta 14a. In the conventional apparatus, as described above, a catheter is inserted up to the aorta 14a to measure the blood flow velocity and volume. A characteristic of the apparatus according to this invention is that a blood flow velocity and blood flow volume in the aorta 14a can be given by putting a cuff around a part of an artery 14f near the periphery (e.g., an upper arm), and based on information of pulse waves detected by retaining the cuff at given pressures, obtaining a blood flow velocity and blood flow volume of the aorta 14a.

2. Basic Structure of the Apparatus

Figure 3:
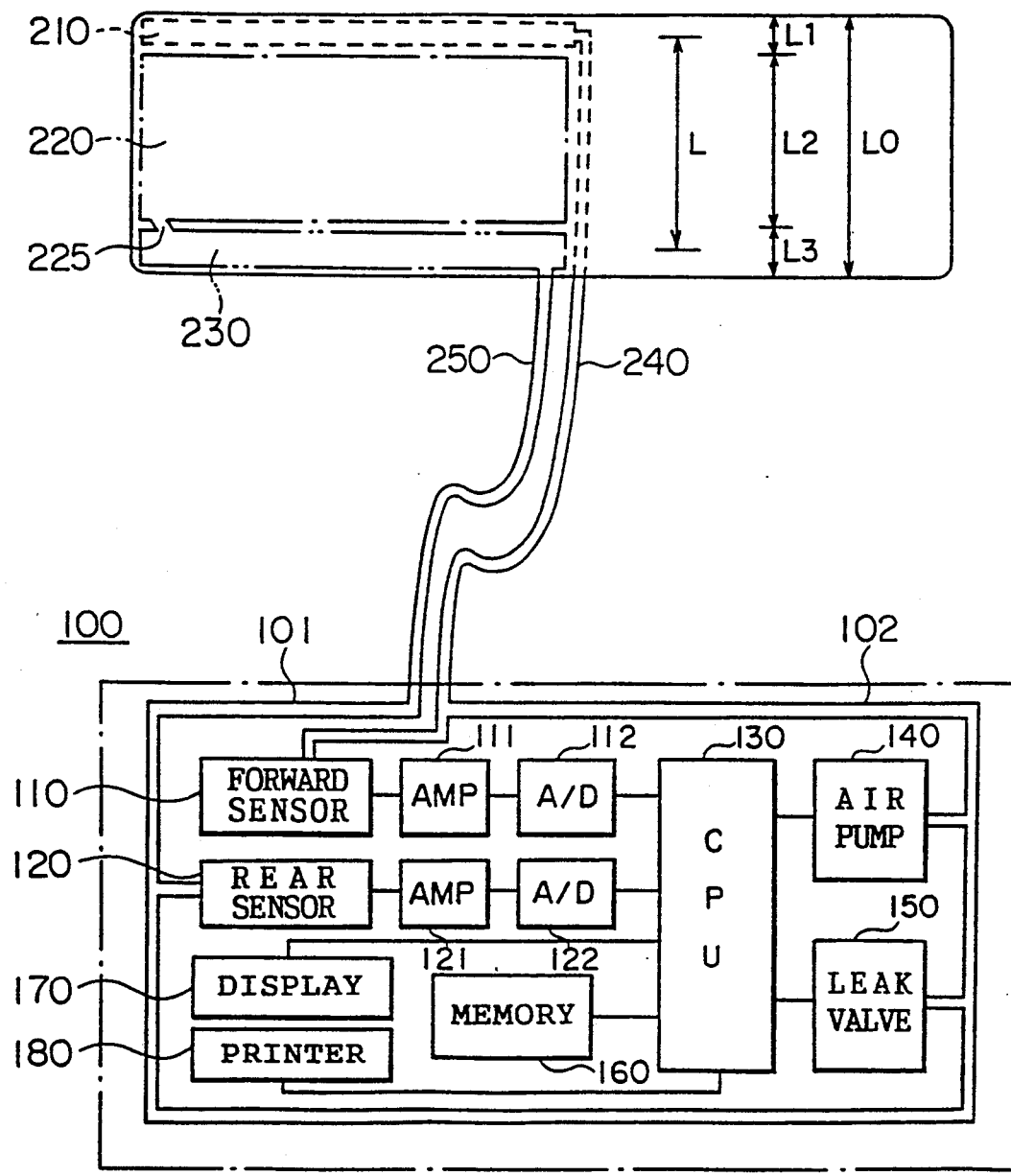
FIG. 3 is a block diagram of the apparatus for measuring a blood flow velocity and a blood flow volume according to this invention.

FIG. 3 is a block diagram of a basic structure of the apparatus for measuring the blood flow velocity and volume according to one embodiment of this invention. This apparatus largely comprises two component parts of an apparatus body 100 (enclosed by an one dot chain line), and a cuff 200. The cuff 200 includes a blood flow shutting bag 220 (indicated by an one dot chain line), a forward detection bag 210 (indicated by a broken line) for detecting a pulse wave heading to the blood flow shutting bag 220, and a rear detection bag 230 (indicated by a two dot chain line) for detecting a pulse wave which has cleared the blood flow shutting bag 220. The blood flow shutting bag 220 has a size sufficient to shut the blood flow, and according to this embodiment, in FIG. 3 the width L2 of the blood flow shutting bag 220 is L2=10 cm vs. the total width of the cuff, L0=14 cm. The forward detection bag 210 and the rear detection bag 230 are sufficiently smaller in comparison with the blood flow shutting bag 220, and according to this embodiment, the width L1 of the forward detection bag 210 is L1=about 1.5 cm, and the width L3 of the rear detection bag 230 is L3=about 2.0 cm. The distance L between the centers of the forward detection bag 210 and of the rear detection bag 230 is L=about 12 cm. This distance L will be an important constant for the determination of a blood flow velocity which will be described below. If the detection bags 210, 230 are too large, it will be impossible to sufficiently detect pulse waves which have impinged on the bags because of their large air volumes. The blood flow shutting bag 220 and the rear detection bag 230 are communicated with each other by an intermediate connection passage 225. A conduit 240 for passing air is extended outside from the forward detection bag 210, and similarly a conduit 250 is extended outside from the rear detection bag 230. This cuff 200 is put around an upper arm as viewed in FIG. 4. When air is fed into the respective bags of the cuff put around in this state to apply a pressure, an artery 300 is pressed by the respective bags as shown in the sectional view of FIG. 5 (in FIG. 5 the respective bags are spaced from one another for the convenience of explanation but less spaced actually in the cuff). When the pressure is raised sufficiently high, the blood flow of the artery 300 is completely shut. In this case, when a pulse wave propagated from the left in FIG. 5 impinges on the forward detection bag 210, and the high frequency component of the pulse wave clears the forward detection bag 210 to impinge on the blood flow shutting bag 220. But because the blood flow shutting bag 220 has a large volume and high resistance, the high frequency component is prevented by the blood flow shutting bag 220 from reaching the rear detection bag 230. When the pulse wave is permitted to clear the blood flow shutting bag 220 as the pressure is decreased, the pulse wave clears the bag 220 to impinge on the rear detection bag 230. Eventually, the forward detection bag 210 is always detecting a pulse wave, but the rear detection bag 230 detects a pulse wave only when the pulse wave clears the blood flow shutting bag 220.

As shown in FIG. 3, the apparatus body 100 has the following structure. A piping 102 connected to the conduit 240 is connected to a forward sensor 110, and a piping 101 connected to the conduit 250 is connected to a rear sensor 120. The forward sensor 110 measures a pressure of the forward detection bag 210, and the rear sensor 120 measures a pressure of the rear detection bag 230. The respective sensors are designed so as to sufficiently detect a frequency band of the pulse wave. An analog signal detected by the forward sensor 110 is amplified by an amplifier 111 and is converted to a digital signal by an A/D converter 112 to be supplied to a CPU 130. Similarly a signal detected by the forward sensor 120 is amplified by an amplifier 121 and is converted to a digital signal by an A/D converter 122 to be supplied to the CPU 130. An air pump 140 and a leak valve 150 are connected to the piping 102. The air pump 140 and the leak valve 150 are controlled by the CPU 130. The piping 101 and the piping 102 are interconnected, and the blood flow shutting bag 220 and the rear detection bag 230 are interconnected by the intermediate passage 225. Accordingly the blood flow shutting bag 220 and the detection bags 210, 230 intrinsically have the same pressure. But because of a large capacity and resistance of the blood flow shutting bag 220, a pressure change of a high frequency is found only by the forward detection bag 210 and the rear detection bag 230. Accordingly it is preferable that the forward sensor 110 and the rear sensor 120 are disposed near the conduit 102 and the conduit 101. A memory 160 for storing data, a display device 170 for displaying the data, and a printer 180 are connected to the CPU 130.

3. Basic Operation of the Apparatus

Figure 6:
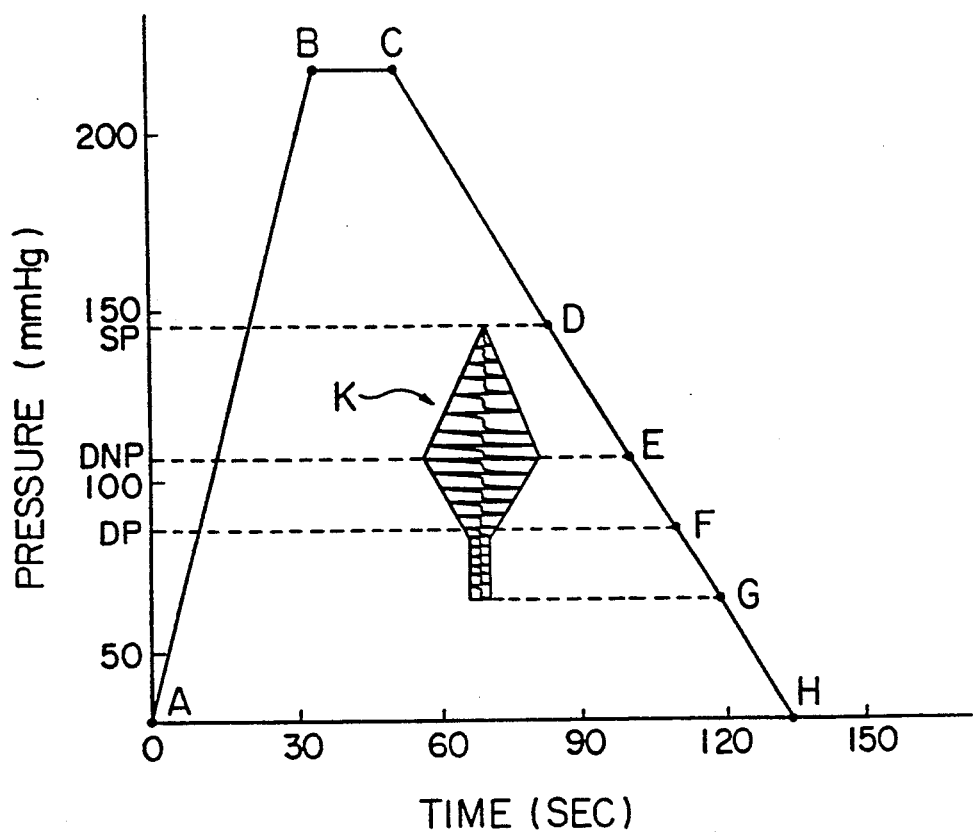
FIG. 6 is a graph explaining the basic operation of the apparatus of FIG. 3.

FIG. 6 shows a graph explaining the basic operation of this apparatus. As described above, this apparatus includes the air pump 140 and the leak valve 150 to control the pressure of the blood flow shutting bag 220 and the detection bags 210, 230. That is, when their pressure is raised, the air pump 140 is actuated to feed air into the bags, and when the pressure is decreased, the leak valve 150 is opened to let out the air in the bags.

Figure 4:
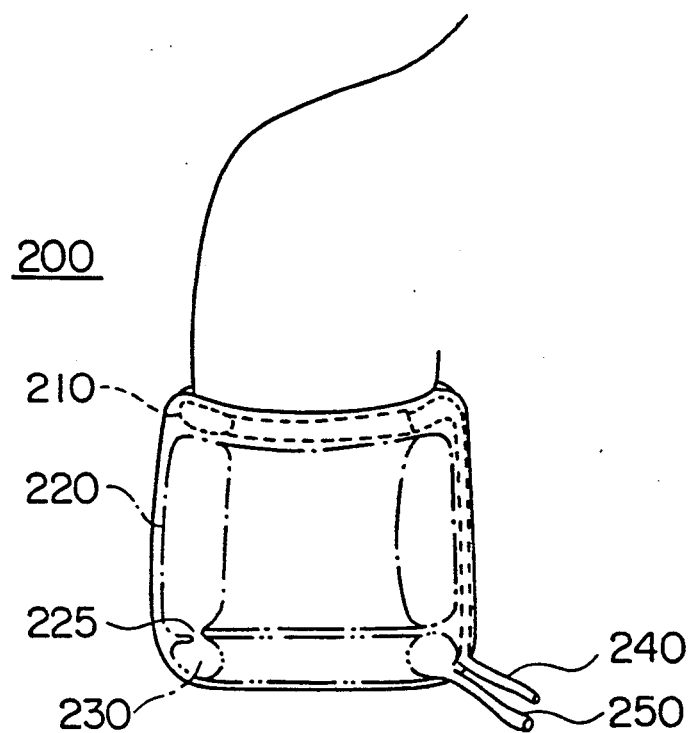
FIG. 4 is a view of the cuff involved in the apparatus of FIG. 3, which is put around an upper arm.
Figure 5:
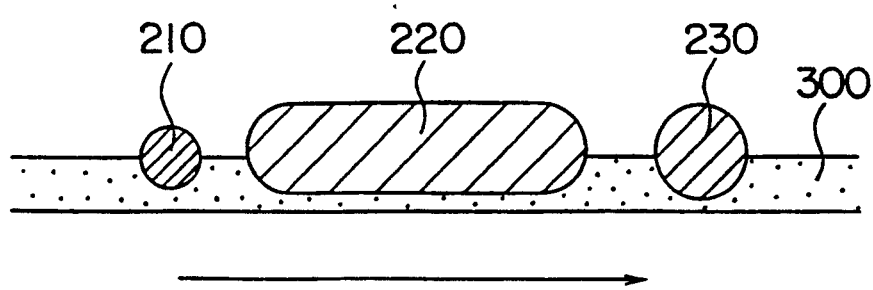
FIG. 5 is a view of the cuff involved in the apparatus of FIG. 3, which is pressing an artery.
Figure 8A:
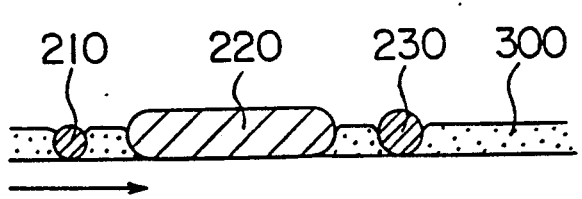
FIGS. 8a to 8e are sectional views showing the relationship between the cuff and the passage of a pulse wave.
Figure 8B:
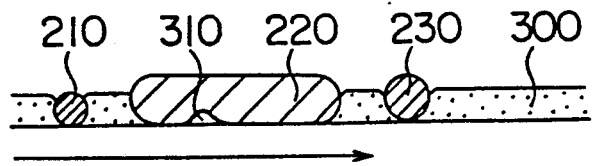
Figure 8C:
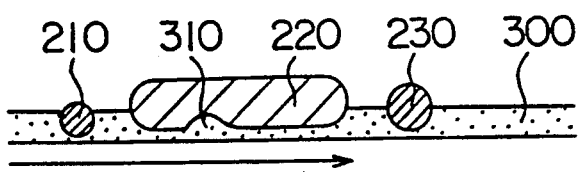
Figure 8D:
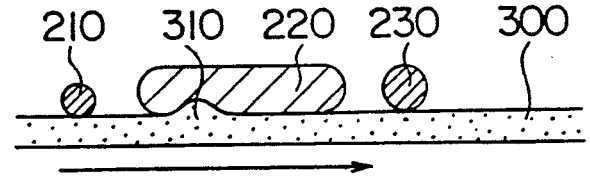
Figure 8E:
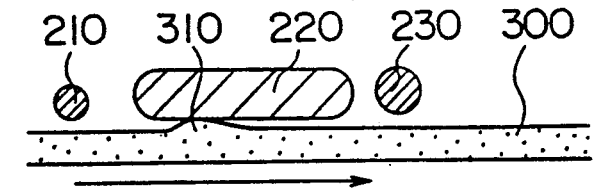

In a measuring operation, the cuff 200 is put around an upper arm of a person to be measured as shown in FIG. 4, and a measurement initiating switch (not shown) is turned on. The graph of FIG. 6 shows changes of a pressure of the bags immediately after the initiation of a measuring operation. That is, when the operation is started, the CPU 130 actuates the air pump 140 to feed air into the bags to gradually raise a pressure in the bags (from Point A toward B in the graph). The blood flow shutting bag 220 gradually presses the artery, and soon its pressure reaches a pressure which completely shuts the blood flow (Point B). The relationship between the cuff 200 (the blood flow shutting bag 220 and both detection bags 210, 230) with the artery 300 at this time is shown by the sectional view of FIG. 8a. The left side of the view is the heart, and the right side of the view is the periphery, and a pulse wave is propagated from the left to the right. As described above, a high frequency component of the pulse wave can clear the forward detection bag 210, but none of the frequency components of the pulse wave can clear the blood flow shutting bag 220 because of a higher pressure of the blood flow shutting bag 220. Accordingly, at this time the forward sensor 110 detects the pulse wave heading to the blood flow shutting bag 220, but the rear sensor 120 can detect none of the pulse wave. The pressure value at this time is maintained for a some time (Points B to C) to confirm the presence of air leakage of the bag. Then the CPU 130 slowly opens the leak valve 150 to decrease the pressure (from Point C toward D). Then a Korotkoff sound is generated at Point D. The waveform K in the graph indicates amplitudes of Korotkoff sounds of respective pulses obtained for respective pressure values when the pressure is gradually decreased from Point D (in this embodiment a sound wave sensor for detecting a Korotkoff sound is not included). It is because a part of the pulse wave 310 begins to clear the blood flow shutting bag 220 against a pressure of the blood flow shutting bag 220 as shown in FIG. 8b that a Korotkoff sound is generated past Point D. It is known that a pressure at Point D is a systolic pressure SP. As the pressure is further decreased from Point D, the pulse wave 310 can clear the blood flow shutting bag 220 with more ease as shown in FIG. 8c, and the Korotkoff sound becomes maximum at Point E. Hereafter, the Korotkoff sound gradually diminishes, and at Point F the Korotkoff sound is very small and continuously has constant amplitudes. It is known that a pressure at Point F is a diastolic pressure DP, and this state corresponds to that of FIG. 8d. As the pressure is further decreased, the Korotkoff sound dies out at Point G, and the pressure finally reaches Point H. At this time the cuff 200 is afloat on the artery 300 as shown in FIG. 8e.

4. Detection of Pulse Wave

Here the method for detecting a pulse wave will be explained. A pulse wave is a change of an internal pressure of the artery 300 and accordingly is measured in a pressure value. As shown in FIGS. 8a to 8e, a pulse wave propagated from the heart impinges first on the forward detection bag 210. The forward sensor 110 detects a pressure change due to this impingement of the pulse wave with the detection bag 210. The rear sensor 230 detects a pressure change due to the impingement of the pulse wave which has cleared the blood flow shutting bag 220. The amplitude of the pulse wave which clears the blood flow shutting bag 220 depends on a pressure of the bag 220.

Figure 7:
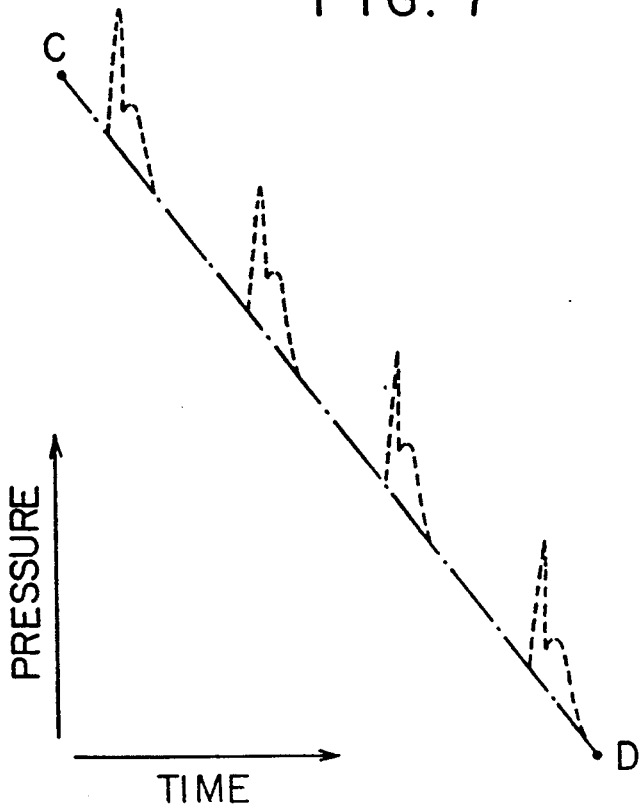
FIG. 7 is a view of a waveform detected by the sensors involved in the apparatus of FIG. 3.

Here when a pressure value per se detected by the forward or the rear sensor 110, 120 is noted, it will be seen that two factors are multiplexed. That is, one is a pressure of the blood flow shutting bag 220, and the other is a pressure change due to a pulse wave generated by the forward detection bag 210 or the rear detection bag 230 (a capacity of the blood flow shutting bag 220 itself is designed so large that a change of its pressure due to the impingement of a pulse wave is negligible). Here the former is called reference internal pressure, and the latter is called pulse wave pressure. Because all the bags are interconnected with one another by the conduits as shown in FIG. 3, all the bags have a reference internal pressure when no pulse wave impinges thereon. The graph of FIG. 6 shows this reference internal presure. Pressures actually detected by the sensors are the reference internal pressure multiplexed with pulse pressures. When this apparatus is operated in accordance with, e.g., the graph of FIG. 6, the reference internal pressure is decreased with time from Point C to Point D as shown in FIG. 6. However, a pressure value detected by the forward sensor 110 is, as shown in FIG. 7, the reference internal pressure (indicated by an one dot chain line) multiplexed with a pulse pressure (indicated by a broken line). Accordingly, the waveform of the pulse wave is given by subtracting the reference internal pressure from the detected pressure value of the sensor 110.

Figure 9:
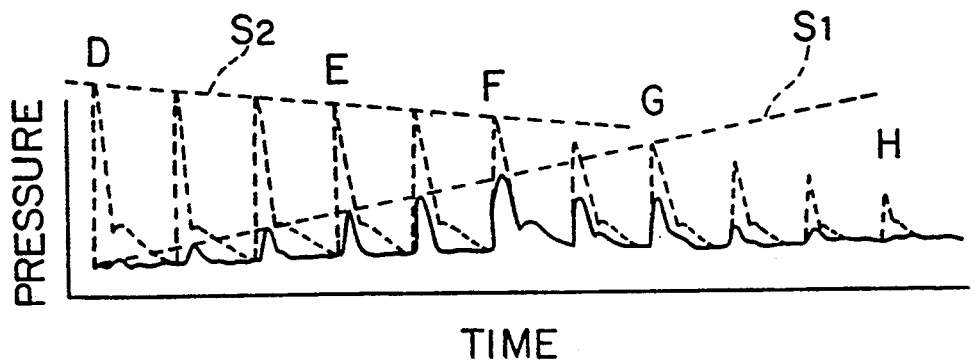
FIG. 9 is a waveform view showing the relationship between the cuff and the detected pulse waves.

FIG. 9 shows various waveforms of pulse waves detected from Point D to Point H in the graph of FIG. 6. The broken line waveforms are of a pulse wave detected by the forward sensor 110 (hereinafter called forward pulse wave). The solid line waveforms are of a pulse wave detected by the rear sensor 120 (hereinafter called rear pulse wave). The letters above the respective pulse waves indicate that the pulse waves were detected at points indicated by the letters in the graph of FIG. 6. The absence of a letter above a pulse wave means that the pulse wave was detected intermediate between points with the letters above. When the solid line rear pulse waves are noted, as a pressure is gradually decreased from Point D, an amplitude of a detected rear pulse wave gradually increases along an auxiliary line S1. At Point F the amplitude becomes maximum, and thereafter the amplitude gradually decreases. On the other hand, when the broken line forward pulse waves are noted, as the pressure is gradually decreased from Point D, the amplitude of a detected pulse wave gradually decreases along the auxiliary line S2. This is because as the blood flow shutting of the bag 220 is gradually released (FIG. 8b), larger parts of the pulse wave increasingly clear the bag 220 to the periphery. After Point F, the amplitude of the pulse wave further decreases. This is because the forward detection bag 210 is afloat on the artery 300 as shown in FIG. 8e.

5. Blood Flow Velocity Measurement Principle I

Next, the blood flow velocity measurement principle on which the apparatus of this invention is based will be explained. This measurement principle is based on a new finding by the inventor of the present application. The inventor has found the following fact. That is, when a cuff is put around an upper arm and a pressure thereof (the reference internal pressure of the bags) is retained at a systolic pressure SP, a velocity at which a pulse wave clears the pressing cuff is approximate to a blood flow velocity VH in the high pressure period T1 (see FIG. 1) of the aorta. In other words, in the circulation passage of FIG. 2, when the pressing cuff is put around a peripheral part 14f and a pressure thereof is retained at a systolic pressure SP so as to shut the blood flow of the artery, a velocity at which a pulse wave clears the cuff is approximate to a blood flow velocity VH of the aorta 14a in the high pressure period. The reason for this fact has not been so far analyzed, but the result of the actual blood flow velocity in the high pressure period obtained by inserting a catheter into the aorta 14a, and the result measured by this apparatus based on the above described measurement principle agree with each other with considerably high experimental precision.

Figure 10:
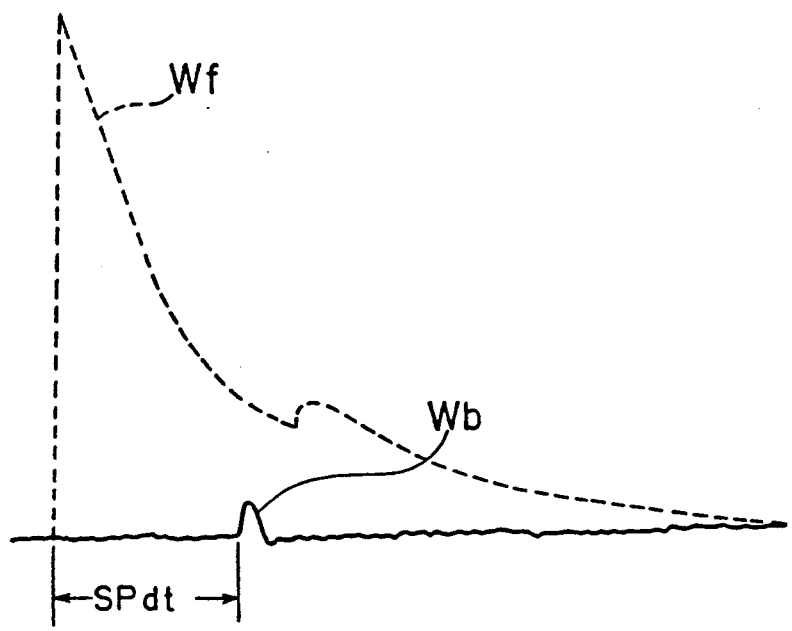
FIG. 10 is a view of a delay time of a rear pulse wave with respect to a forward pulse wave.
Figure 11:
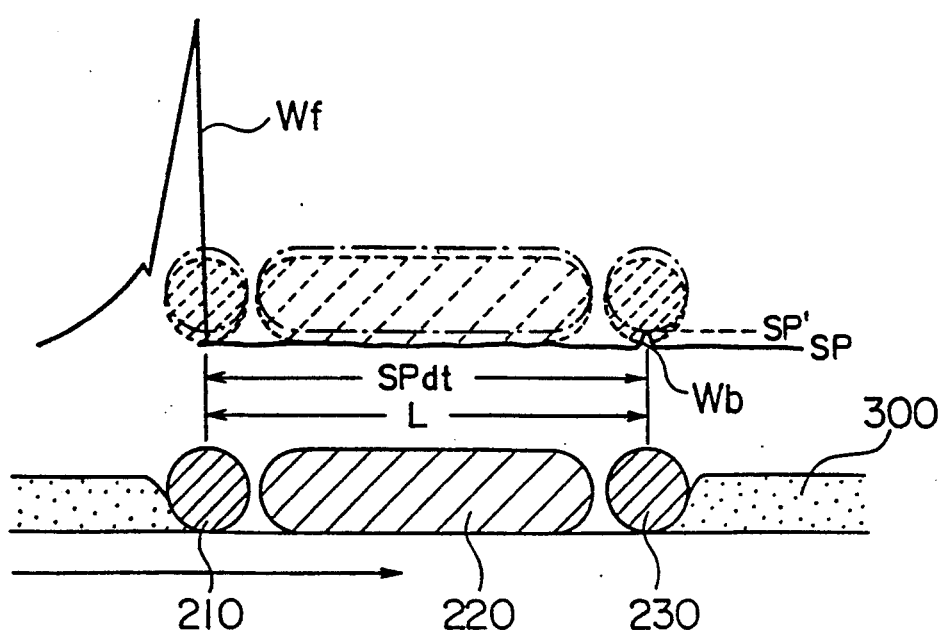
FIG. 11 is a view of the passage of a pulse wave when a cuff pressure is equal to a systolic pressure.

For the measurement of a blood flow velocity of the aorta in the high pressure period, based on this innovational measurement principle, the apparatus according to this embodiment is operated as follows. The cuff 200 is put around an upper arm of a person to be mesured, and the reference internal pressure of the respective bags is changed to those at Points A, B, C and D along the graph of FIG. 6. When the pressure reaches Point D, a pressure at this time (a systolic pressure SP) is retained for some time. The arrival of the pressure at Point D can be recognized by the rear sensor 120 beginning to detect a rear pulse wave. When the pressure has reached Point D, a time difference between a forward pulse wave detected by the forward sensor 110, and a rear pulse wave detected by the rear sensor 120 is measured. When the reference internal pressure is a systolic pressure SP (corresponding to Point D in the graph of FIG. 6), a detected forward pulse wave and a detected rear pulse wave are shown by the broken line pulse wave and the solid line wave pulse, respectively, at Point D in FIG. 9 as described before. FIG. 10 shows an enlarged view of these pulse waves. The rising position of the solid line rear pulse wave Wb is offset from that of the broken line forward pulse wave WF by a delay time SPdt. The reason for the occurrence of this delay time is explained clearly in FIG. 11. FIG. 11 shows at the lower part a sectional view of the artery 300 whose blood flow is shut by the respective detection bags 210, 220, 230 having the reference internal pressure retained at a systolic pressure SP. When a pulse wave is propagated from the left to the right, the pulse wave first impinges on the forward detection bag 210. A part of the pulse wave clears the pressing blood flow shutting bag 220 to impinge on the rear detection bag 230. The detected pulse wave at this time is shown upper in FIG. 11. The broken line positions of the detection bags indicate those of the detection bags retained at the reference internal pressure (a systolic pressure SP). The one dot chain line positions of the detection bags indicate those of the detection bags pushed up by the passing pulse wave (at this time a detected pressure is SP'). Thus, the forward pulse wave Wf is detected by the forward detection bag 210, and the rear pulse wave Wb is detected by the rear detection bag 230. Since FIG. 11 shows a state of a pulse wave being propagated from the left to the right, the waveform of the pulse wave is horizontally reversed to that in FIG. 10 (in FIG. 10 time is taken on the horizontal axis, but in FIG. 11 spacing is taken on the horizontal axis). As seen in FIG. 11, the rear pulse wave Wb is propagated over a distance L to be detected by the rear detection bag 230. Accordingly the rear pulse wave Wb is detected behind the forward pulse wave Wf by a delay time SPdt which the pulse wave takes to travel. Here since the distance L is a constant given as a distance between the centers of the forward detection bag 210 and of the rear detection bag 230, a propagation speed Vsp of the rear pulse wave Wb is given by $$Vsp = L/SPdt \qquad (1).$$

The inventor of the present application has thus found that the propagation speed Vsp is approximate to a blood flow velocity VH of the aorta in the high pressure period. In this way, this apparatus enables an approximate value of a blood flow velocity of the aorta in the high pressure period to be given.

In addition, the inventor of the present application has also confirmed that a propagation velocity Vdp of a pulse wave clearing the pressing cuff when the pressure of the cuff (the reference internal pressure of the bags) is retained at a diastolic pressure DP is equal to a pulse wave propagation velocity at a part with the cuff put around. Accordingly by conduction the same measurement as described above with the reference internal pressure retained at a diastolic pressure DP, a pulse wave propagation velocity can be also measured.

6. Blood Flow Velocity Measurement Principle II

The principle of measuring a blood flow velocity VH of the aorta in the high pressure period T1 is as described above. Here the principle of measuring a blood flow velocity VL in the low pressure period T2 will be explained. The inventor of the present application has found an simple method for giving a blood flow velocity VL in the low pressure period, based on a blood flow velocity VH in the high pressure period. According to this simple method, a blood flow velocity VL can be given by the following simple calculation using a conversion coefficient R.

$$VL = VH/R \qquad (2)$$

where $$R = (SP - DP)/(DNP - DP) \qquad (3).$$

In these Equations, SP, DP and DNP respectively represent a systolic pressure, diastolic pressure and dicroticnotch pressure. The reason for such a simple calculation being applicable has not been yet analyzed in detail. But the inventor of the present application thinks as follows. When the aortic wave of FIG. 1 is considered, in the high pressure period T1, a pressure difference (SP−DP) generated by a contraction of the heart causes blood to be sent out of the heart. On the other hand, in the low pressure period T2, because the aortic valve is closed, blood flows due to the Windkessel action in the aorta, and this is considered to result from a pressure difference (DNP−DP). Accordingly, when the conversion coefficient R is defined as in equation (3), a blood sending out pressure in the high pressure period T1 is R times a blood sending out pressure in the low pressure period T2. Since it is considered that a blood flow velocity increases in proportion to a pressure for sending out blood, it is natural to consider that a blood flow velocity in the high pressure period T1 is R times a blood flow velocity in the low pressure period T2. Thus, a blood flow velocity VL in the low pressure period can be given using Equation (2). A blood flow velocity VL thus given by the conversion and the result of the actual measurement obtained by inserting a catheter into the aorta agree with each other with considerably high experimental precision.

Here to obtain a blood flow velocity VL in the low pressure period T2 by the above described method, it is necessary to know pressure values DP, SP, DNP. This apparatus has a function of detecting an approximate aortic wave as shown in FIG. 1, and these pressure values can be given from the approximate aortic wave. The function of detecting an approximate aortic wave will be explained later in good detail.

7. Blood Flow Volume Measuring Principle

Subsequently, the blood flow volume measuring principle on which the apparatus of this invention is based is described. This measurement principle is also based on a new finding made by the inventor of the present application. Generally a flow volume Q of a fluid travelling through a pipe is given as a product of a velocity V of the fluid and an effective sectional area S of the pipe by the following equation $$Q = S \times V \qquad (4).$$

Accordingly a blood flow volume Q per pulse is given by the following equation $$Q = SH \times VH + SL \times VL \qquad (5).$$

In Equation (5), SH and SL represent blood flow effective sectional areas respectively in the high pressure period T1 and in the low pressure period T2, and VH and VL represent blood flow velocity respectively in the high pressure period T1 and in the low pressure period T2. Since the blood flow velocities VH, VL can be given by the above described methods, a blood flow volume Q per pulse can be calculated by Equation (5) if blood flow effective sectional areas SH, SL are known.

Then the blood flow effective sectional area of the aorta will be considered. A characteristic of the blood flow results from periodic pulse waves. When it is assumed that the section of the aorta is perfectly circular, the sectional area of this circle varies with time, based on aortic waves. This will be explained with reference to FIG. 12. A section of the aorta is shown on the left side of FIG. 12, and on the right side is shown an aortic wave WA. At a time t1 the heart is in its expanded state.

The pressure of the vessel wall of the aorta has a diastolic pressure DP. Here it is assumed that the section of the aorta is an rDP radius circle as shown on the left side of FIG. 12, Soon, the heart contracts, and at a time t2 the pressure of the vessel wall of the aorta is raised to a systolic pressure SP. It is assumed that resultantly the aorta is expanded, and the vessel section becomes an rSP radius circle. When time has further passed, the aorta shrinks with a decrease of the pressure, and at a time t5, the vessel section of the aorta returns to the rDP radius circle. In other words, the vessel section of the aorta follows the process of expanding from the rDP radius circle to the rSP radius circle at every pulse of the heart, and returning to the rDP radius circle.

Figure 12:
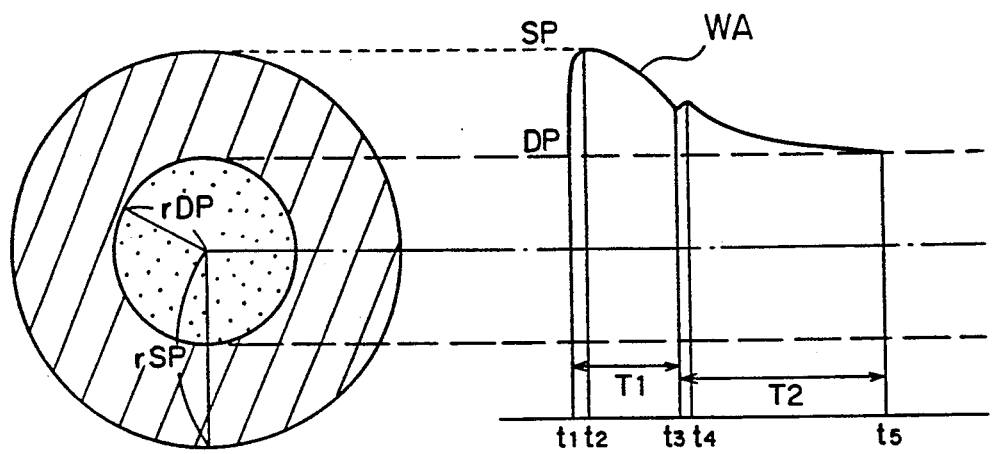
FIGS. 12 and 13 are views explaining the principles for giving a blood flow effective sectional area to be used in the calculation of a blood flow volume, based on waveforms of pulse waves.
Figure 13:
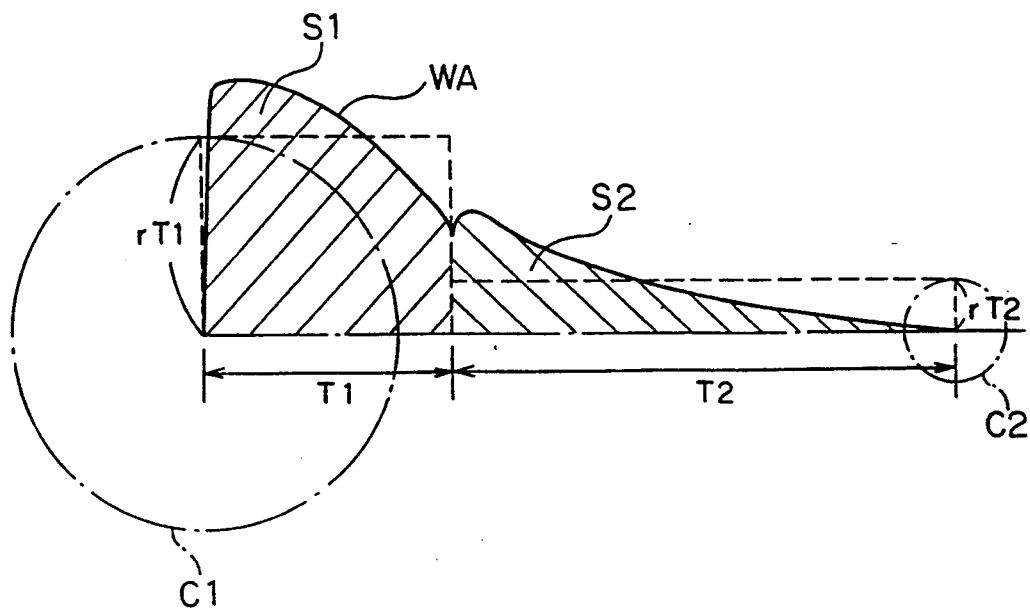

In the vessel section of the aorta shown on the left side of FIG. 12, the hatched portion with oblique lines is an expanded region due to a pulse wave. It is considered that only this region is a blood flow effective section which contributes to the flow of the blood. This is because only pulse waves cause the blood to flow. Without pulse waves, the section of the aorta is the shaded portion with dots in FIG. 12 (inside of the rDP radius circle), and the blood stagnates in this portion. Accordingly a blood flow effective area is an area of the hatched portion with oblique lines, and this area varies with a time and in accordance with an aortic wave WA. Then, blood flow effective sectional areas SH in the high pressure period T1 and that SL in the low pressure period T2 are given as follows. First, as shown in FIG. 13, an aortic wave WA is bisected in two portion of the high pressure period T1 and the low pressure period T2, and integrated values S1, S2 for the respective portions (corresponding to an area of the hatched portion with oblique lines) are calculated. Next, effective radii rT1, rT2 are calculated by $$rT1 = S1/T1 \quad (6)$$

$$rT2 = S2/T2 \quad (7).$$

Then it can be considered that the blood flow effective section for the high pressure period T1 is an rT1 radius circle C1, and that for the low pressure period T2 is an rT2 radius circle C2. That is, although the blood flow effective sectional area actually varies incessantly with time, an average blood flow effective sectional area SH for the high pressure period T1 and that SL for the low pressure period T2 can be defined as follows.

$$SH = \pi \times rT1^2 \quad (8)$$

$$SL = \pi \times rT2^2 \quad (9).$$

When the blood flow effective sectional areas SH, SL are thus given, a blood flow volume Q per pulse can be given by Equation (5). By multiplying a blood flow volume Q with a pulse number per minute, a blood flow volume Qm per minute can be given.

In FIG. 13, since the vertical axis value of the aortic wave WA is actually given in the unit of pressure (mmHg), the radius values rT1, rT2 for determining a blood flow effective sections are in the unit of pressure unless converted. Then, it is necessary for the actual calculation to convert values in the unit of pressure (mmHg) to a unit of length (mm). A coefficient to be used in this conversion may be experimentally determined beforehand. That is, a blood flow effective sectional area and an aortic wave are measured on one person with a conventional method, whereby, based on a relationship between the two, a conversion coefficient can be determined.

8. Approximate Aortic Wave Detection Principle

Innovational methods for measuring the blood flow velocity and blood flow rate of an aorta have been explained above. These methods have to use the detection results of an aortic wave. Conventionally aortic waves have been detected by invasive methods in which catheters are inserted in aortas. But in the apparatus according to this invention, a waveform approximate to an aortic wave can be non invasively detected. Another application was filed on the apparatus for detecting this approximate aortic wave (filed May 17, 1990 in the Japanese Patent Office by the same person as the applicant of the present application as an international application PCT/JP90/00623 "APPARATUS FOR DETECTING AND DISPLAYING BLOOD CIRCULATORY INFORMATION" based on Patent Cooperation Treaty). The contents of said another application is described in good detail in its specification, and only its basic principle will be briefed in this specification.

As shown in FIG. 2, the pulse wave of the upper arm (e.g., the pulse wave WF) is different from the aortic wave WA. But the inventor of the present application has found that a pulse wave detected by the rear detection bag 230 when the blood flow shutting bag 220 is retained at a diastolic pressure DP is approximate to an aortic wave although the pulse wave is detected on the upper arm. It is difficult to theoretically analyze the reason for this precisely, but the inventor of the present application thinks that the blood flow shutting bag 220 functions as a low pass filter to cut off a high frequency component of the pulse wave. As shown in FIG. 2, a pulse wave has a high frequency component increased as it further travels to the periphery. But it is thought that the high frequency component is cut off when the pulse wave (pulse wave WF) of an upper arm clears the blood flow shutting bag 220 and is filtered into a pulse wave approximate to an aortic wave WA. Accordingly it is necessary that the blood flow shutting bag 220 has a width sufficient to function as the low pass filter, but it has been experimentally confirmed that for this function its width equal to or larger than 9 cm is sufficient for the general standard body. Since a pulse wave approximate to an aortic wave can be obtained when a pressure of the blood flow shutting bag 220 is equal to a diastolic pressure DP, the reference internal pressure is maintained constant when it has reached a diastolic pressure DP at Point F in the graph of FIG. 6, and a rear pulse wave is detected while the reference internal pressure is being maintained at the diastolic pressure DP. The detected rear pulse wave can be taken as an aortic wave. That is, in FIG. 9, the rear pulse indicated by the solid line at F is an approximate aortic wave.

Here, in operating this apparatus in accordance with the graph of FIG. 6, how it is judged whether or not Point F has been reached, i.e., a pressure value has decreased to a diastolic pressure DP. In this apparatus a very unique method is used. To explain this method, FIG. 9 will be again referred to FIG. 9 is a view of forward pulses (broken line) and rear pulses (solid line) obtained when a pressure value of a blood flow shutting bag 220 is changed. FIG. 9 suggests an effective method for judging whether the reference internal pressure of the cuff has reached Point F, i.e., whether or not a pressure value has decreased to a diastolic pressure DP.

That is, a forward pulse wave (broken line) and a rear pulse wave (solid line) detected at Point F have the lower parts perfectly agreed with each other. Reversely, it can be said that when both pulse waves have the lower parts perfectly agreed with each other, the reference internal pressure of the cuff is a diastolic pressure DP.

Figure 14:
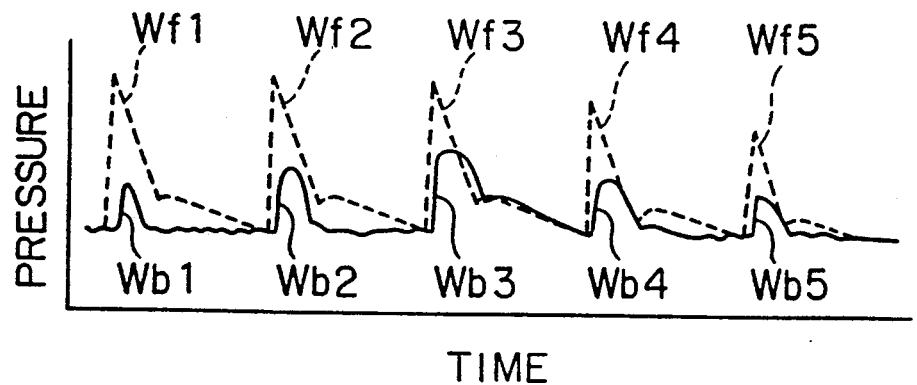
FIG. 14 is a view comparing a forward pulse wave and a rear pulse wave.
Figure 15:
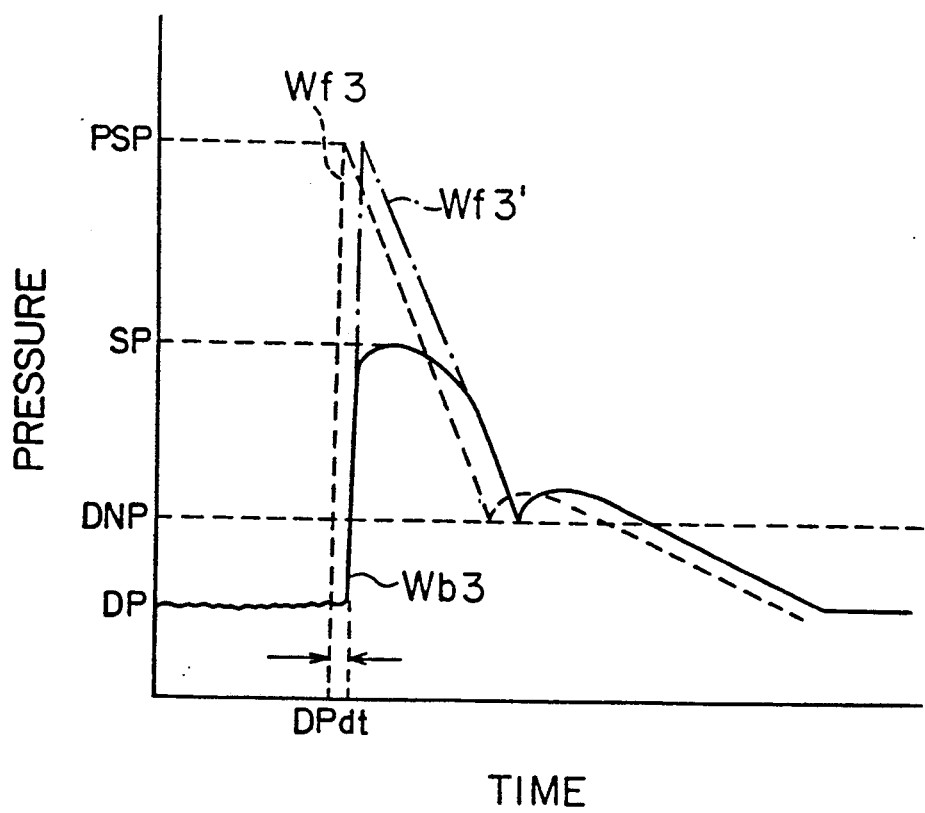
FIG. 15 is a partially enlarged view of FIG. 14.

Actually to compare with both pulse waves, a delay time of the rear pulse wave has to be considered. That is, as described above, the forward pulse wave and the rear pulse wave are not concurrently detected. Accordingly, when forward pulse waves Wf1 to Wf5 and rear pulse waves Wb1 to Wb5 are respectively compared on the same time axis as shown in FIG. 14, they are respectively offset from each other by a delay time. Then it is necessary to delay the forward pulse waves to multiplex the rear pulse waves with the forward pulse waves with the rising parts of both pulse waves agreed with each other and to compare the lower parts of both pulse waves. FIG. 15 is a view explaining the comparison between the forward pulse wave Wf3 and the rear pulse wave Wb3 in good detail. The rear pulse wave Wb3 is behind the forward pulse wave Wf3 by a delay time DPdt, but the forward pulse wave Wf3 is moved to Wf3' so that the rising parts of both pulse waves agree with each other, and the lower parts of the pulse wave Wf3' and the pulse wave Wb3 are compared with each other. In this embodiment, the parts of pulse waves below a dicroticnotch pressure DNP are compared as the lower parts. In the example of FIG. 15 the part of the waveforms below the dicroticnotch pressure DNP are in perfect agreement with each other. But since actually such perfect agreement cannot be expected, it is preferable that agreements with a given error (e.g., an error equal to or lower than ±3%) are judged "Agreement". A rear pulse wave obtained at a time when "Agreement" is thus judged is an approximate aortic wave.

9. Actual Measuring Operation

So far the blood flow velocity measurement principle, the blood flow volume measurement principle and the approximate aortic wave detection principle have been separately explained above. Here the actual measuring operation of the apparatus of FIG. 3 will be explained. With reference to the graph of FIG. 6, the basic operational procedure of this apparatus will be briefly repeated. First the cuff 200 is put around an upper arm of a person to be measured, the leak valve 150 is closed, and the air pump 140 is actuated to gradually raise the reference internal pressure of the cuff until the reference internal pressure reaches Point B from Point A. Then the air pump 140 is stopped, and a given time is taken from Point B to Point C to confirm that there is no air leakage. Subsequently the leak valve 150 is opened at Point C to decrease the reference internal pressure at a given rate (e.g., 2 mmHg/sec) from Point C to Point H. On the way from Point C to Point H, at Point D (where the reference internal pressure has reached a systolic pressure SP), and at Point F (where the reference internal pressure has reached a diastolic pressure DP) the following processing is performed.

First, at Point D, a propagation velocity of a pulse wave clearing the cuff is obtained. The propagation velocity is given as a quotient obtained by dividing a distance L between the forward detection bag 210 and the rear detection bag 230 by a delay time SPdt of a rear pulse wave with respect to a forward pulse wave. This velocity is a high pressure period blood flow velocity VH of the aorta. The arrival of the reference internal pressure at Point D is recognized at a time when the rear detection bag 230 detects the pulse wave for the first time.

Next, waveform of the rear pulse wave at point F is recorded as a waveform of the approximate aortic wave. The arrival of the reference internal pressure at Point F is recognized by the agreement of the lower part of the forward pulse wave with that of the rear pulse wave with a given precision.

Then a mere calculation processing follows the above described processing to determine all the necessary values. That is, since a diastolic pressure DP and a systolic pressure SP have been already given, and an approximate waveform of an aortic wave has been recorded, a dicroticnotch pressure DNP and pressure values in the high and low pressure periods T1, T2 can be determined. A low pressure period blood flow velocity VL can be given by Equation (2), and a blood flow volume per pulse Q is given by Equation (5). These calculations are conducted by the CPU 130 and their results are displayed by a display device 170. Their results can be also outputted to the printer 180 as required.

Figure 16:
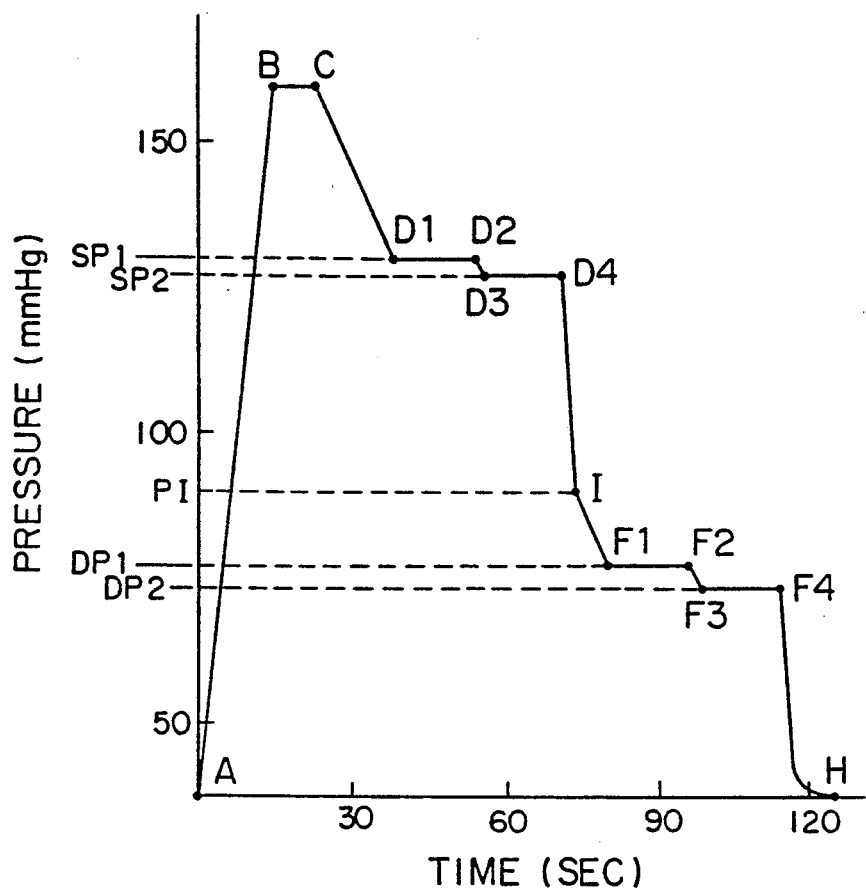
FIG. 16 is a graph of the actual measuring operation of the apparatus of FIG. 3.

Thus, basically by performing the measuring operation along the graph of FIG. 6, intended values can be obtained. Actually, however, the measuring operation along the graph of FIG. 6 cannot provide measured values of high precision. To obtain measured results of higher precision, it is necessary to input more data obtained at Points D and F of the graph. Then it is preferable to make the actual measuring operation along the graph of FIG. 16. The measuring operation based on the graph of FIG. 16 is basically the same as that based on the graph of FIG. 6. But the measurements at Points F and D are conducted more elaborately. First, the cuff 200 is put around an upper arm of a person to be measured, the leak valve 150 is closed, and the air pump 140 is actuated, so that a pressure of the cuff is increased from Point A of the graph of FIG. 16 to Point B thereof. Then the air pump 140 is stopped for some time from Point B to Point C to confirm that there is no air leakage. The operation up to here is quite the same as that of the measuring operation based on the graph of FIG. 6. Subsequently the leak valve is opened to lower the pressure at a constant velocity (e.g., 2 mmHg/sec).

At Point C, the forward sensor 110 detects a forward pulse wave, but the rear sensor 120 has not yet detected a rear pulse wave. But as the pressure is lowered, soon the rear sensor 120 detects a rear pulse wave for the first time. This point is Point D1 of the graph. When a rear wave pulse is detected for the first time, the CPU 130 closes the leak valve 150 to retain a pressure SP1 at this time for a given measuring period (Point D1 to Point D2 of the graph). When this period has passed, the leak valve 150 is instantaneously opened so as to lower the pressure by a trace of amount (e.g., 3 mmHg), and again this pressure SP2 is maintained for a given measuring period (Point D3 to Point D4 of the graph). This operation is repeated until a condition for determining a systolic pressure SP (which will be explained later) is satisfied (repeated twice in the graph of FIG. 16). When the condition for determining a systolic pressure SP is thus satisfied, the leak valve 150 is again opened to lower pressure (Point D4 toward I of the graph). In this embodiment, for the purpose of shortening a time which the procedure of a measuring operation takes, the pressure is rapidly lowered from Point D4 to Point I (e.g., 10 mmHg/sec), and after the pressure has passed Point I, the pressure is decreased at a usual velocity (e.g., 2 mmHg/sec). A pressure value PI at Point I is $$PI = SP2 - dP \qquad (10)$$

In this equation, a pressure value dP is preset constant (e.g., 30 mmHg). Since a next job of the CPU 130 is to recognize a diastolic pressure DP, the pressure is rapidly lowered from Point D4 to Point I so that a diastolic pressure DP can be obtained fastly. At Point I, the lower parts of the forward pulse wave and of the rear pulse wave have not yet agreed with each other. But as the pressure is lowered, soon the agreement within a set error range is detected between both pulse waves. This is found at Point F1. When the agreement within a set error range is found for the first time, the CPU 130 closes the leak valve 150 to maintain a pressure DP1 at this time for a set measuring period of time (from Point F1 to Point F2). When the measuring period has passed, the leak valve 150 is instantaneously opened to lower the pressure by a trace of amount (e.g., 3 mmHg), and again a pressure DP2 is retained for a set measuring period of time (Point F3 to Point F4 in the graph). This operation is repeated until the condition for determining a diastolic pressure DP (which will be explained later) is satisfied (repeated twice in the graph of FIG. 16). When the condition for determining a diastolic pressure DP is satisfied, the leak valve 150 is opened to decrease the pressure rapidly (Point F4 to Point H in the graph). What has been described above is the total procedure of the actual measuring operation of this apparatus.

Figure 17:
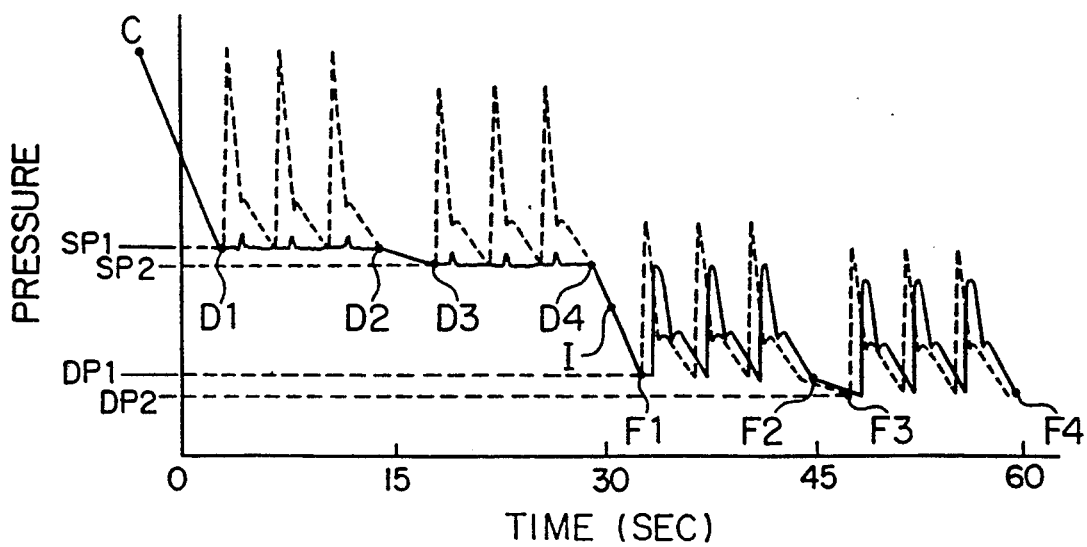
FIG. 17 is a view of pulse waves detected by the actual measuring operation of FIG. 17.
Figure 18A:
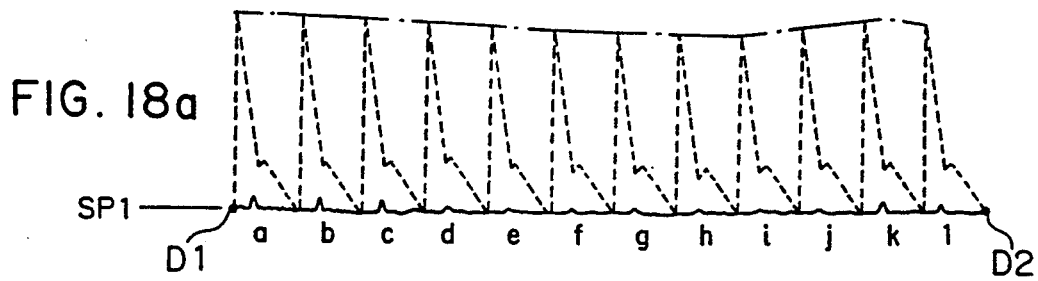
FIGS. 18a, 18b, 19a, and 19b are partially enlarged views of FIG. 17.
Figure 18B:
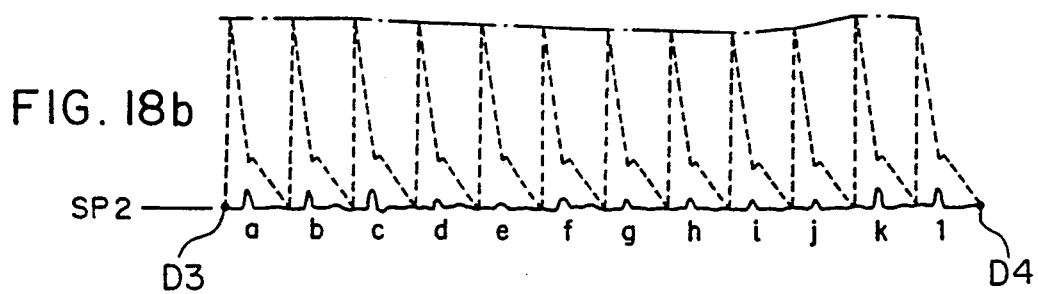
Figure 19A:
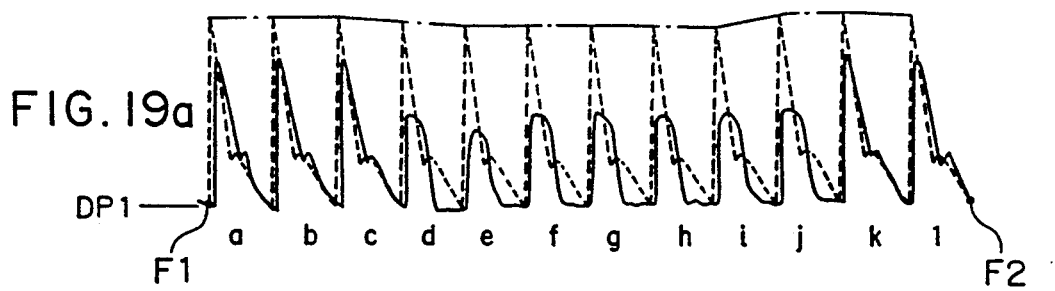
Figure 19B:
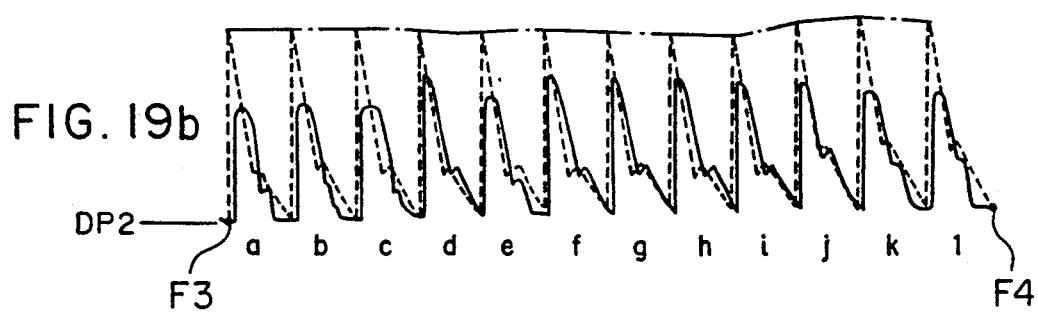

Subsequently detection results of the above described measuring operation by the respective sensors will be discussed. FIG. 17 is a graph of pressure values detected by the respective sensors in accordance with the measuring operation shown in the graph of FIG. 16. In the graph of FIG. 17, Points C, D1 to D4, I, and F1 to F4 correspond to the respective points in the graph of FIG. 16, and the broken line depicts forward pulse waves detected by the forward sensor 110, and the solid line depicts rear pulse waves detected by the rear sensor 120. In the example of FIG. 17, a set measuring period of time in which a pressure is retained constant is a period corresponding to three pulses, but actually it is preferable to set a period of time of 10 or more pulses. FIGS. 18a to 19b show detection results for measuring periods of time each of 12 pulses. FIG. 18a is a graph of pulse waves detected in Periods D1 to D2, FIG. 18b is a graph of pulse waves detected in Periods D3 to D4, FIG. 19a is a graph of pulse waves detected in Periods F1 to F2, and FIG. 19b is a graph of pulse waves detected in Periods F3 to F4. In the respective graphs forward pulse waves are depicted by borken lines, and rear pulse waves are depicted by solid lines. When periods of 12 pulse waves are successively measured, the detected pulse waves have deviations although a pressure of the cuff is maintained constant. In the graphs the one dot chain line connecting the peak positions of the forward pulse waves clearly indicate the deviations. These deviations largely result from respirations of a person to be measured. Accordingly to obtain measuring results of high precision, it is preferable to set a measuring period of at least one respiration period.

Because of such deviations, the determination of a systolic pressure SP is performed by the following method. First, a pressure is gradually lowered from Point C in the graph of FIG. 16 to recognize Point D1 where a rear pulse wave is detected for the first time. The judgement "whether or not a rear pulse wave has been detected" is actually to judge whether or not the peak value of a pulse wave outputted from the rear sensor 120 has exceeded a set "detection threshold value". When Point D1 is recognized, a pressure SP1 at Point D1 is maintained for a measuring period of time 12 pulses (Points D1 to D2). The passage of this period of time can be recognized easily by counting 12 forward pulse waves. The pulse waves detected during this period of time are as shown in FIG. 18a. The forward pulse waves (broken lines) are clearly detected, but the rear pulse waves (solid lines) are so small that all the rear pulse waves have not exceeded a "detection threshold value". Here it is assumed that in FIG. 18a, five pulse waves a, b, c, k, 1 out of 12 rear pulse waves have exceeded a "detection threshold value". Then a detection accuracy is 5/12. Thus a detection accuracy is obtained, and when a detection accuracy exceeds a preset detection accuracy, the condition for determining a systolic pressure SP has been satisfied. If the allowance for the detection accuracy is preset at 8/12, the above described measurement at SP1 has not satisfied the condition for determining a systolic pressure SP. Then the pressure value is slightly lowered to repeat the measurement at a pressure SP2. One example of results of this measurement is shown in FIG. 18b. Because a pressure of the cuff is a little lowered, a pulse wave can clear the pressing cuff with more ease, and a little generally larger pulse wave can be detected. If it is assumed that at this time eleven pulse waves out of 12 rear pulse waves a to 1 except a rear pulse wave e have exceeded a "detection threshold value", the detection accuracy is 11/12, which exceeds an allowance of 8/12. Accordingly the condition for determining a systolic pressure SP has been satisfied. The measuring operation can proceed to a next measuring step for determining a diastolic pressure DP. A value of systolic pressure SP, which is finally determined, is an average of pressure values SP1 and SP2. A delay time SPdt to be used in determining a high pressure period blood flow velocity VH in an aortic wave is an average between a delay time obtained in the measurement at the pressure SP1 and a delay time obtained in the measurement at the pressure SP2.

Quite similarly the determination of a diastolic pressure DP is performed by the following method. The pressure is gradually lowered from Point I in the graph of FIG. 16 to recognize Point F1 where the lower parts of both pulse waves agree with each other within a set allowance for error. The pressure DP1 at this point is maintained, and a measuring period of time 12 pulses is taken (Point F1 to Point F2). The passage of this measuring period of time can be easily recognized by counting twelve forward pulse waves. The pulse waves detected during this measuring period of time are exemplified in FIG. 19a. All twelve pairs of forward and rear pulse waves do not always exhibit the agreement within the set allowance for error. Here it is assumed that only five pairs a, b, c, k, 1 out of twelve pairs of pulse waves a to 1 have exhibited the agreement. The agreement accuracy is 5/12. An allowance value for this agreement accuracy is preset, and when an agreement accuracy exceeds this allowance, it is judged that the condition for determining a diastolic pressure DP is satisfied. If the allowance for the agreement accuracy is set at 8/12, the above described measurement at the pressure DP1 has not yet satisfied the condition for determining the diastolic pressure DP. Then the pressure is a little lowered to repeat the measurement at the pressure DP2. One example of results of this measurement is shown in FIG. 19b. Here it is assumed that six pairs d, f, g, h, i, j out of twelve pairs of pulse waves a to l have exhibited the agreement. The agreement accuracy for this measuring period is 6/12, which still below the allowance 8/12. But As seen by comparing FIG. 19a with FIG. 19b, the pairs a, b, c, k, l, which exhibited the agreement at the pressure DP1 do not exhibit the agreement at the pressure DP2. In other words, although the pairs of pulses a, b, c, k, l do not exhibit the agreement at the pressure DP2, these pairs have already exhibited the agreement at the pressure DP1. The reason for this will be seen in FIG. 9. In FIG. 9, pulse waves of a pair at Letter F exhibit the agreement, but neither the right next pair nor the left next pair exhibits the agreement. That is, when it once has passed a pressure where a forward pulse wave and a rear pulse wave exhibit the agreement, they never again exhibit the agreement. Accordingly it is necessary to accumulatively treat the agreement accuracy. That is, the agreement accuracy of the measurement at the pressure DP1 is 5/12, that at the pressure DP2 being 6/12, and the accumulated agreement accuracy of both measurements is 11/12 which exceeds the allowance 8/12. Accordingly it is judged that the condition for determining the diastolic pressure DP has been satisfied. The entire process of a measuring operation by this apparatus is over. A final value of the diastolic pressure DP can be an average of the pressures DP1 and DP2. The waveform of an approximate aortic wave can be an average of a plurality of rear pulse waveforms.

10. Output of Measurement Results

Various data can be obtained by the above described measuring operation. The data are stored in the memory 160 so that effective data for diagnoses can be displayed on the display device 170 or can be outputted to the printer 180. In the apparatus according to this embodiment, the following information are outputted as the measuring results.

(1) A blood flow velocity VH in a high pressure period and a blood flow velocity VL in a low pressure period of an aorta.

(2) A systolic pressure SP, a diastolic pressure DP, and a dicroticnotch pressure DNP.

(3) A blood flow effective sectional area SH in a high pressure period and a blood flow effective sectional area SL in a low pressure period of an aorta.

(4) A blood flow volume per pulse Q.

(5) A number of pulses per minute n (given by counting forward pulse waves).

(6) A blood flow volume per minute Qm (Qm=Qxn).

(7) A body surface area BSA of a person to be measured (when a height H and a weight W of a person are measured and inputted, it is given by $BSA = W^{0.45} \times H^{0.75}$).

(8) A pulse coefficient CI (given by CI=Qm/BSA).

11. Other Embodiments

As described above, this invention has been explained by means of an embodiment shown in the drawings. It is possible to embody this invention in other various modes. For example, in the above described embodiment, a systolic pressure SP and a diastolic pressure DP are recognized based on pulse waves detected by the pressure sensors. But is is possible to recognize them based on Korotkoff sounds detected by a sound wave sensor. That is, as indicated by the waveform K in FIG. 6, as the cuff pressure is decreased, at a systolic pressure SP a Korotkoff sound begins to be generated, and then the pressure exceeds a diastolic pressure DP the amplitude of the korotkoff sound becomes constant. Accordingly by monitoring the Korotkoff sounds by a sound wave sensor, the arrival at a systolic pressure SP and a diastolic pressure DP can be recognized.

INDUSTRIAL APPLICABILITY

The blood flow velocity and blood flow volume measuring apparatus disclosed in the present application is usable for the diagnosis of circulation diseases. Since this apparatus can provide measurement results simply by putting around the cuff on an upper arm and is very useful compared with the conventional invasive measuring methods. This invention will much contribute to the present medical diagnostic technology.

I claim:

1. An apparatus for measuring a blood flow velocity in an aorta, comprising:
   a cuff (200) including a blood flow shutting bag means (220) for shutting a blood flow of an upper arm, a forward detection bag means (210) for detecting a pulse wave heading to the blood flow shutting bad, means and a rear detection bag means (230) for detecting a pulse wave which has cleared the blood flow shutting bad means;
   pressure control means (130, 140, 150) for retaining a reference internal pressure of the blood flow shutting bag means and the respective detection bag means at a systolic pressure SP;
   forward sensor means (110) for detecting as a forward pulse wave (Wf) a pressure change generated in the forward detection bag means;
   rear sensor means (120) for detecting as a rear pulse wave (Wb) a pressure change generated in the rear detection bag means with a delay time SPdt from a detection time of the forward pulse wave;
   calculating means (130) for dividing a distance L between the forward detection bag means and the rear detection bag means by the delay time SPdt to obtain a quotient, and outputting the quotient as a blood flow velocity VH of an aorta in a high pressure period.

2. An apparatus according to claim 1, further comprising means for obtaining a systolic pressure SP, a diastolic pressure DP, a dicroticnotch pressure DNP, calculating a coefficient R based on Equation R=(SP−DP)/(DNP−DP), calculating a quotient by dividing the blood flow velocity VH in the high pressure period by the coefficient R, and outputting the quotient as a blood flow velocity VL in the aorta in a low pressure period.

3. An apparatus for measuring a blood flow velocity in an aorta, comprising:
   a cuff (200) including a blood flow shutting bag means (220) for shutting a blood flow of an upper arm, a forward detection bag means (210) for detecting a pulse wave heading to the blood flow shutting bag means, and a rear detection bag means (230) for detecting a pulse wave which has cleared the blood flow shutting bag means;
   forward sensor means (110) for detecting as a forward pulse wave (Wf) a pressure change generated in the forward detection bag means;
   rear sensor means (120) for detecting as a rear pulse wave (Wb) a pressure change generated in the rear detection bag means with a delay time dt from a detection time of the forward pulse wave;

pressure control means (130, 140, 150) for gradually decreasing a reference internal pressure of the blood flow shutting bag means and the respective detection bags means from a sufficiently high pressure for shutting a blood flow, and retaining the reference internal pressure as a pressure SP when the rear sensor means detects a rear pulse wave for a first time; and means (130) for, while the pressure control means is retaining the reference internal pressure at the pressure SP, obtaining a delay time SPdt of the rear pulse wave with respect to the forward pulse wave, calculating a quotient by dividing a distance L between the forward detection bag means and the rear detection bag means by the delay time SPdt, and outputting the quotient as a blood flow velocity VH of the aorta in a high pressure period.

4. An apparatus for measuring a blood flow velocity in an aorta, comprising:

a cuff (200) including a blood flow shutting bag means (220) for shutting a blood flow of an upper arm, a forward detection bag means (210) for detecting a pulse wave heading to the blood flow shutting bag means, and a rear detection bag means (230) for detecting a pulse wave which has cleared the blood flow shutting bag means;

a forward sensor means (110) for detecting as a forward pulse wave (Wf) a pressure change generated in the forward detection bag means;

a rear sensor means (120) for detecting as a rear pulse wave (Wb) a pressure change generated in the rear detection bag means with a delay time dt from a detection time of the forward pulse wave;

agreement judging means (130) for delaying the forward pulse wave by the delay time dt to superpose the forward pulse wave on the rear pulse wave, and judging whether or not lower parts of both the pulse waves agree with each other with a set precision;

pressure control means (130, 140, 150) for gradually decreasing a reference internal pressure of the blood flow shutting bag means and the respective detection bag means from a sufficiently high value for shutting a blood flow, retaining the reference internal pressure as a pressure SP during a first period when the rear sensor means detects a rear pulse wave for a first time, gradually decreasing the reference internal pressure after the first period of time is over, and retaining the reference internal pressure as a pressure DP during a second period when the agreement judging means agrees;

means (130) for obtaining a delay time SPdt of the rear pulse wave with the forward pulse wave in the first period, dividing a distance L between the forward detection bag means and the rear detection bag means by the delay time SPdt to calculate a quotient, and outputting the quotient as a blood flow velocity of the aorta in a high pressure period; and means (130) for recognizing a rear pulse wave detected by the rear sensor means in the second period as an approximate aortic wave near a heart, obtaining a systolic pressure SP, a diastolic pressure DP and a dicroticnotch pressure DNP based on the approximate aortic wave, calculating a coefficient R based on Equation $R=(SP-DP)/(DNP-DP)$, calculating a quotient by dividing the blood flow velocity VH in the high pressure period by the coefficient R, and outputting the quotient as a blood flow velocity VL of the aorta in a low pressure period.

5. An apparatus for measuring a blood flow volume in an aorta, comprising:

a cuff (200) including a blood flow shutting bag means (220) for shutting a blood flow of an upper arm, a forward detection bag means (210) for detecting a pulse wave heading to the blood flow shutting bag means, and a rear detection bag means (230) for detecting a pulse wave which has cleared the blood flow shutting bag means;

pressure control means (130, 140, 150) for retaining a reference internal pressure of the blood flow shutting bag means and the respective detection bag means at a systolic pressure SP and a diastolic pressure DP;

a forward sensor means (110) for detecting as a forward pulse wave (Wf) a pressure change generated in the forward detection bag means;

a rear sensor means (120) for detecting as a rear pulse wave (Wb) a pressure change generated in the rear detection bag means with a delay time dt from a detection time of the forward pulse wave;

means (130) for obtaining a delay time SPdt of the rear pulse wave with the forward pulse wave when the reference internal pressure is retained at the systolic pressure SP, dividing a distance L between the forward detection bag means and the rear detection bag means by the delay time SPdt to calculate a quotient, and giving the quotient as a blood flow velocity VH of the arota in a high pressure period; and means (130) for recognizing a rear pulse wave detected when the reference internal pressure is retained at the diastolic pressure DP as an approximate aortic wave, obtaining a blood flow effective sectional area SH of the aorta in the high pressure period based on a waveform of the approximate aortic wave before a dicroticnotch, and multiplying the blood flow velocity VH in the high pressure period with the blood flow effective sectional area SH in the high pressure period to give a blood flow volume in the high pressure period.

6. An apparatus according to claim 5, further comprising means (130) for obtaining a systolic pressure SP, a diastolic pressure DP, a dicroticnotch pressure DNP based on the recognized approximate aortic wave, calculating a coefficient R based on Equation $R=(SP-DP)/(DNP-DP)$, dividing the blood flow velocity VH in the high pressure period by the coefficient R to calculate a blood flow velocity VL of the aorta in a low pressure period, obtaining a blood flow effective sectional area SL of the aorta in the low pressure period based on a waveform of the approximate aortic wave after the dicroticnotch, and multiplying the blood flow velocity VL in the low pressure period with the blood flow effective area SL in the low pressure period to give a blood flow volume in the low pressure period.

7. An apparatus for measuring a blood flow volume in an aorta, comprising:

a cuff (200) including a blood flow shutting bag means (220) for shutting a blood flow of an upper arm, a forward detection bag means (210) for detecting a pulse wave heading to the blood flow shutting bag means, and a rear detection bag means (230) for detecting a pulse wave which has cleared the blood flow shutting bag means;

a forward sensor means (110) for detecting as a forward pulse wave (Wf) a pressure change generated in the forward detection bag means;

a rear sensor means (120) for detecting as a rear pulse wave (Wb) a pressure change generated in the rear detection bag means with a delay time dt from a detection time of the forward pulse wave;

agreement judging means (130) for delaying the forward pulse wave by the delay time dt to superpose the forward pulse wave on the rear pulse wave, and judging whether or not lower parts of both the pulse waves agree with each other with a set precision;

pressure control means (130, 140, 150) for gradually decreasing a reference internal pressure of the blood flow shutting bag means and the respective detection bag means from a sufficiently high value for shutting a blood flow, retaining the reference internal pressure as a pressure SP during a first period when the rear sensor means detects a rear pulse wave for a first time, gradually decreasing the reference internal pressure after the first period of time is over, and retaining the reference internal pressure as a pressure DP during a second period when the agreement judging means agrees;

means (130) for obtaining a delay time SPdt of the rear pulse wave with the forward pulse wave in the first period, dividing a distance L between the forward detection bag means and the rear detection bag means by the delay time SPdt to calculate a quotient, and outputting the quotient as a blood flow velocity VH of the aorta in a high pressure period; and means (130) for recognizing a rear pulse wave detected by the rear sensor means in the second period as an approximate aortic wave near a heart, obtaining a systolic pressure SP, a diastolic pressure DP and a dicroticnotch pressure DNP based on the approximate aortic wave, calculating a coefficient R based on Equation $R=(SP-DP)/(DNP-DP)$, calculating a quotient by dividing the blood flow velocity VH in the high pressure period by the coefficient R, and outputting the quotient as a blood flow velocity VL of the aorta in a low pressure period;

means (130) for obtaining a blood flow effective sectional area SH of the aorta in the high pressure period based on a waveform of the approximate aortic wave before a dicroticnotch, and multiplying the blood flow velocity VH in the high pressure period with the blood flow effective sectional area SH in the high pressure period to give a blood flow volume in the high pressure period; and means (130) for obtaining a blood flow effective sectional area SL of the aorta in the low pressure period based on the waveform of the approximate aortic wave after the dicroticnotch, and multiplying the blood flow velocity VL in the low pressure period with the blood flow effective sectional area SL in the low pressure period to give a blood flow volume in the low pressure period.

* * * * *